(12) United States Patent
Hobby et al.

(10) Patent No.: US 7,751,051 B2
(45) Date of Patent: Jul. 6, 2010

(54) METHOD FOR CROSS INTERFERENCE CORRECTION FOR CORRELATION SPECTROSCOPY

(75) Inventors: James Hobby, Crowborough (GB); Martin Lopez, Rotherfield (GB)

(73) Assignee: Servomex Group Limited, East Sussex (GB)

( * ) Notice: Subject to any disclaimer, the term of this patent is extended or adjusted under 35 U.S.C. 154(b) by 590 days.

(21) Appl. No.: 11/539,962

(22) Filed: Oct. 10, 2006

(65) Prior Publication Data

US 2007/0114417 A1 May 24, 2007

(30) Foreign Application Priority Data

Nov. 23, 2005 (GB) .................................. 0523817.5

(51) Int. Cl.
 *G01N 21/00* (2006.01)
(52) U.S. Cl. ........................................ 356/437; 356/451
(58) Field of Classification Search .................. 356/51, 356/437, 306–307, 451; 250/338.5, 339.12–339.13, 250/343, 365, 372
See application file for complete search history.

(56) References Cited

U.S. PATENT DOCUMENTS

| | | | |
|---|---|---|---|
| 3,488,491 A | * | 1/1970 | Schuman .................... 250/345 |
| 3,793,525 A | | 2/1974 | Burch et al. |
| 3,811,776 A | | 5/1974 | Blau, Jr. |
| 3,904,880 A | | 9/1975 | Benz et al. |

FOREIGN PATENT DOCUMENTS

| FR | 2 618 554 A1 | 1/1989 |
|---|---|---|
| GB | 2 113 833 A | 8/1983 |

OTHER PUBLICATIONS

Lee et al.; "Gas Filter Correlation Instrument for the Remote Sensing of Gas Leaks;" American Institute of Physics; Rev. Sci. Instrum. 56 (9); Sep. 1985, pp. 1812-1819.
European Search Report for EP 06 254 372.3 dated Apr. 2, 2007.
Examination Report for EP 06 254 372.3 dated Jul. 6, 2009.
Response to Examination Report of Jul. 6, 2009 for EP 06 254 372.3 dated Jan. 18, 2010.

* cited by examiner

*Primary Examiner*—Tarifur Chowdhury
*Assistant Examiner*—Tara S Pajoohi
(74) *Attorney, Agent, or Firm*—Daly, Crowley, Mofford & Durkee, LLP

(57) ABSTRACT

Correlation spectroscopy measure is improved by correcting for cross interference. This is achieved through applying different gains to the output signals whereby the effect of background interferent species can be calculated and an automatic correction factor applied.

11 Claims, 7 Drawing Sheets a) N2 sample gas b) N2 sample gas (gained)

c) NO in N2 sample gas d) NO in N2 sample gas (gained)

▧ = signal with N2 cuvette        ▨ = signal with NO cuvette $I_{oN2}$ = signal for nitrogen (nitrogen in sample gas)
$I_{oNO}$ = signal for NO (nitrogen in sample gas)
$I_{N2}$ = signal for nitrogen (NO in sample gas)
$I_{NO}$ = signal for NO (NO in sample gas)
$G$ = gain factor $I_{N2}$ = signal for nitrogen cuvette (NO in sample gas)
$I_{NO}$ = signal for NO (NO in sample gas)
$I_{off}$ = baseline offset
$G$ = gain factor

METHOD FOR CROSS INTERFERENCE CORRECTION FOR CORRELATION SPECTROSCOPY

CROSS REFERENCE TO RELATED APPLICATIONS

This application claims priority under 35 U.S.C. §119 to Great Britain patent application No. GB 0523817.5 filed on 23 Nov. 2005, which is incorporated herein by reference.

STATEMENT REGARDING FEDERALLY SPONSORED RESEARCH

Not Applicable

FIELD OF THE INVENTION

The present invention relates to a method and apparatus for correcting or reducing cross interference in filter correlation and more particularly correction spectroscopy measurement.

BACKGROUND OF THE INVENTION

Optical absorption measurements have long been used to measure the concentration of a component in a mixture. The absorption behaviour can be described by the Beer-Lambert law. A simple form of an absorption spectrometer consists of a light source, a means to select the relevant wavelength range, a sample chamber and detector. The reduction in the transmitted light intensity when the absorbing component is present allows the concentration of the component to be deduced. Whilst this may give sensitive readings for the component of interest, depending on the absorption strength and path length, it may be subject to zero and sensitivity errors due to changes in the source intensity and cross interference (measurement error) if other components are present which also absorb within the wavelength pass band.

Zero and sensitivity errors can occur because there is no reference to the change in intensity of the source with time. This effect can be compensated for by using a reference measurement which monitors the source output simultaneously with the measurement of interest. The cross interference can be minimised by using a selective detection system, tuned to the specific absorption of the component of interest.

Another approach is by using a single optical path gas filter correlation measurement. The basic lay-out of which is illustrated in FIG. 1. In this method, light from a broad band source 1 is mechanically modulated using a wheel 2 containing a cuvette 3 filled with non-significantly absorbing gas, such as nitrogen and another cuvette 4 containing the gas of interest. In order to increase the signal to noise ratio, an optical band pass filter 5 is used to select a region of interest. The resultant modulated emission is directed into a measurement cell 7, where further absorption may occur, depending on the sample composition. The signal is collected at an optical detector 8 where it is converted into an electrical signal, which is then processed by processing circuitry 9 to produce an external output signal.

The signal from the optical detector will consist of modulated output corresponding to the throughput from the different gas filled cuvettes. The following will describe the simplified case of a single, non-absorbing cuvette filled with nitrogen and a single, absorbing cuvette filled with the gas of interest, in this case, NO (nitric oxide). Although this simple illustration is given, this description applies equally well to any material being measured by any spectroscopic technique such as using absorption or reflection.

Returning to our example, a schematic of the output signals is illustrated in FIGS. 2a and b for the case of non-absorbing mixture (nitrogen) in the sample cell. The signal which has gone through the NO cuvette will always have a smaller amplitude than the signal through the nitrogen cuvette, since some of the light corresponding to the absorption spectrum has been absorbed. Different gains are applied to the two signals, by the processing circuitry 9 such that the magnitudes of the two signals are matched. This is taken as the zero point in deriving the concentration measurements.

Thereafter, when a sample containing the gas of interest is introduced to the sample cell, for example NO in a nitrogen background, a change in the output signal occurs (FIGS. 2c and d). The change in the nitrogen cuvette signal is always larger than that of the NO cuvette, since the NO cuvette has already pre-absorbed a portion of the radiation corresponding to the NO absorption bands. The amount of incident radiation absorbed by the NO cuvette will depend on, for example, its concentration, temperature, background gas and absorption path length. The difference between the two gained signals, $\Delta I$ in FIG. 2d, is related to the NO concentration in the sample gas cell and so this sets the sensitivity for the measurement. The difference is normally divided by the NO cuvette signal to give a normalised signal, which is independent of any changes in the source intensity and then multiplied by an instrumentation factor to give an NO concentration reading.

In the preceding example, the effect of background interferent gas(es) can cause an error in the reading if they absorb within the pass band of the filter. The example described above provides for two types of interference to occur: positive interference, which causes a positive error, where the interferent absorption coincides with an NO absorption bands and negative interference, which causes a negative error, where the absorption does not coincide with an absorption band. This is illustrated in FIG. 3. Positive interference results from an inherent inability to distinguish between NO and the interferent, but negative cross interference results from the normalised differential gain applied to the signals (i.e. proportional to (G-1), where G is the normalised differential gain applied). Often both types of interference can occur simultaneously.

The magnitude of the cross interference for a particular gas mixture can be minimised through choice of the pass band of the optical filter and characteristics of the gas cuvettes. However, in some cases, such as with water as an interferent gas for NO, it may not possible to remove the interference satisfactorily, resulting in unacceptable error.

A common method of dealing with the effect of cross interference is to independently measure the concentration of the cross interferer, whether by gas filter correlation or other means, and correct accordingly. This, of course, requires extra equipment for a second measurement together with increased cost and complexity. Additionally, the sample would not be identical to that seen by the primary measurement, but could have temporal and/or spatial separation.

BRIEF DESCRIPTION OF THE DRAWINGS

In order that the present invention be more readily understood, an embodiment will now be described by way of example with reference to the accompanying drawings, in which.

DETAILED DESCRIPTION OF THE INVENTION

The present invention does not rely on a second measurement, but uses information already present in the signal. It intentionally varies the differential gain applied to the signals by changing the baseline reference in order to create an auto-correction function for the effect of background gases. The positive cross interference is unaffected by any change in the baseline reference, since this is proportional to the relative strength of the absorption overlap of the interferent and NO absorption lines and hence taken out in the calibration. The negative cross interference, however, will be affected by the baseline reference, since this will change differential gain which needs to be applied.

The preferred embodiment utilises the same basic equipment as the prior art and this is shown in FIG. I and the operation is basically the same. However, if a measurement is taken simultaneously or sequentially using two or more baseline references (i.e. two different gains), then two different signals will result. The degree of mismatch between the two signals when no interferent is present can be determined during calibration and any subsequent change in this mismatch gives a measurement of the background interferent concentration. This will hold true whether the interferent is present on its own, or in addition to NO. This system can also be used for the correction for multiple cross interferents. This method presupposes that negative cross interference is always present. However, in reality, this will normally be the case, since two different compounds will not have the same spectral characteristics.

Figure 1:
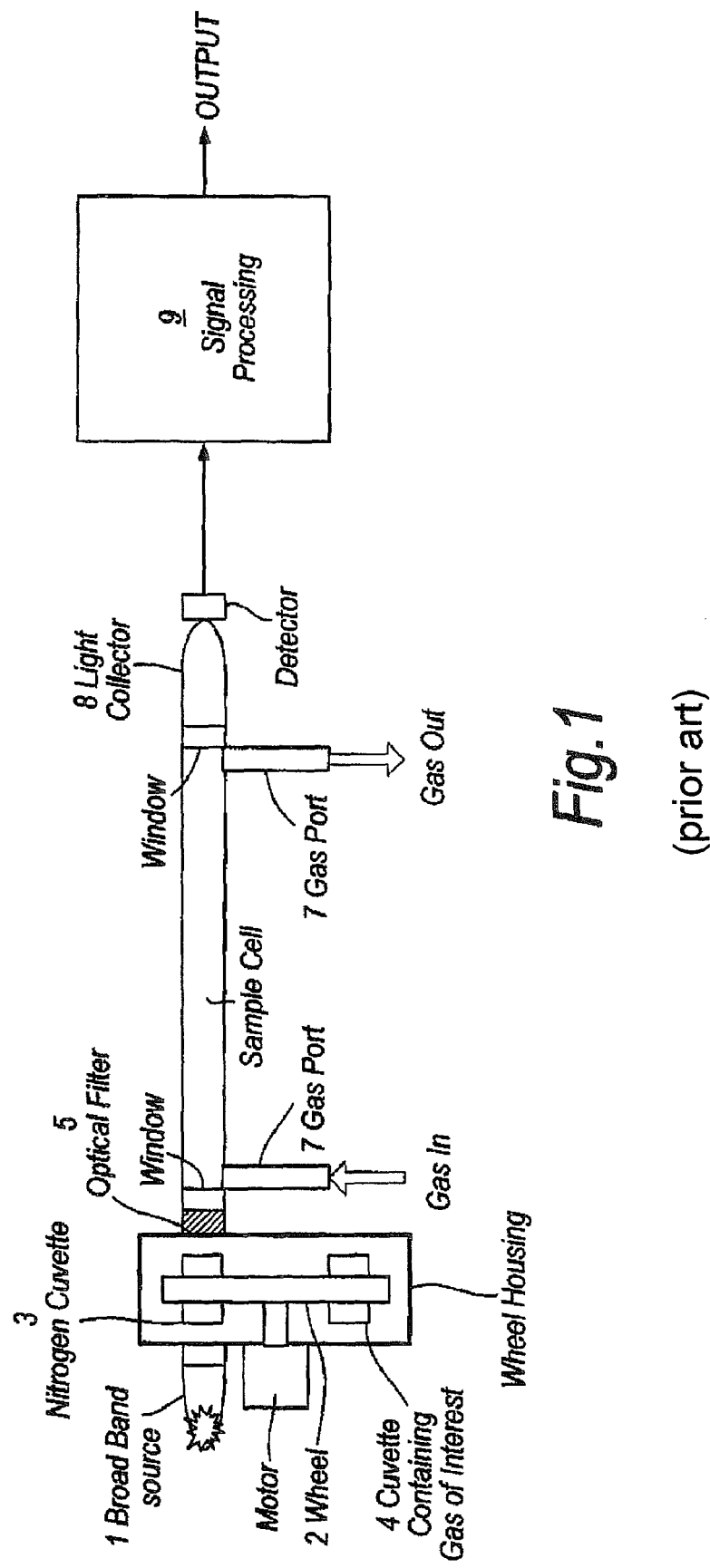
FIG. 1. shows a diagrammatic representation of the basic apparatus for spectroscopic measurement.
Figure 2:
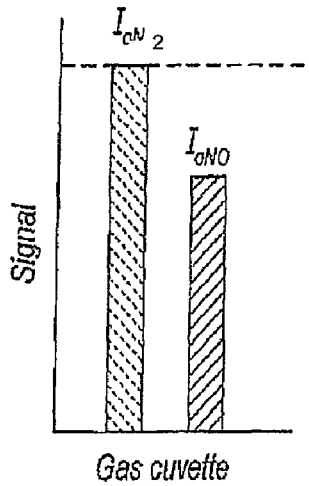
FIGS. 2 and 3 are diagrams aiding the explanation of a prior art method of using apparatus shown in FIG. 1.
Figure 2:
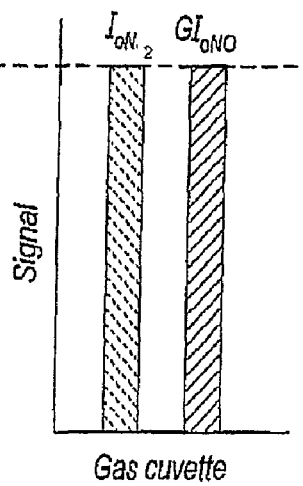
Figure 2:
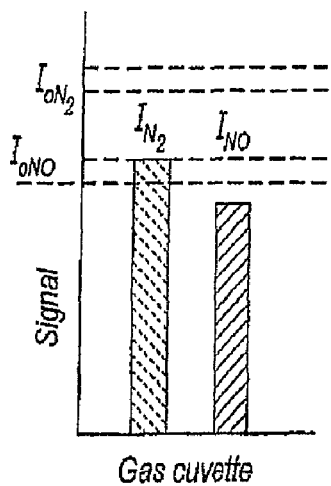
Figure 2:
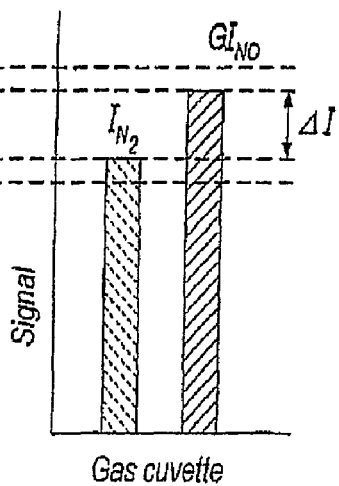
Figure 3:
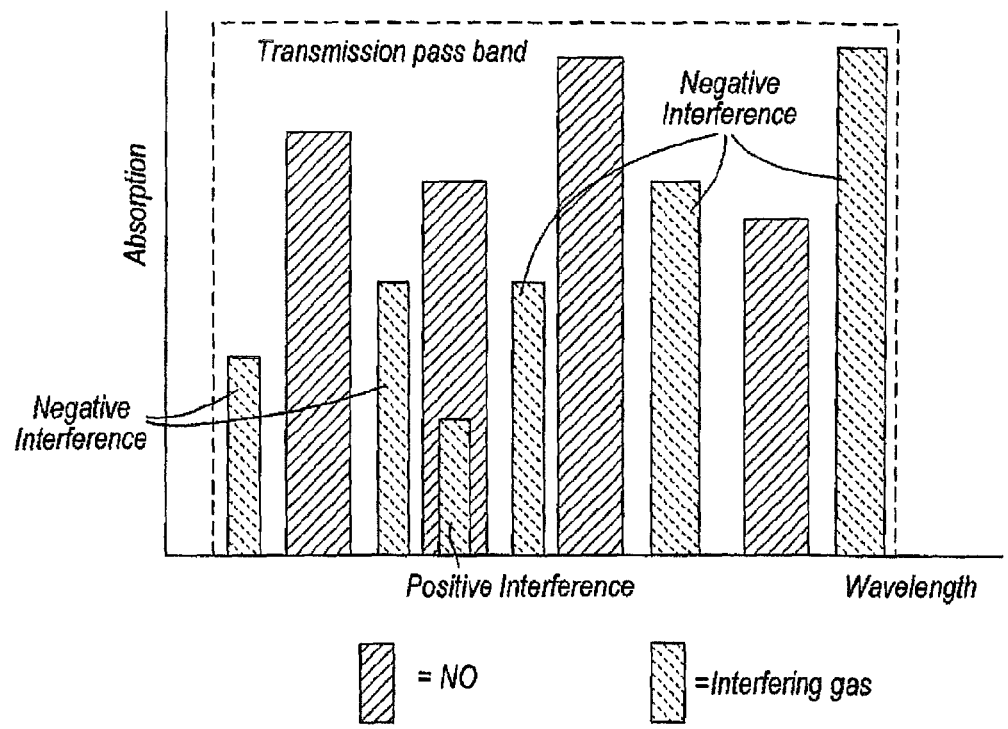
Figure 4:
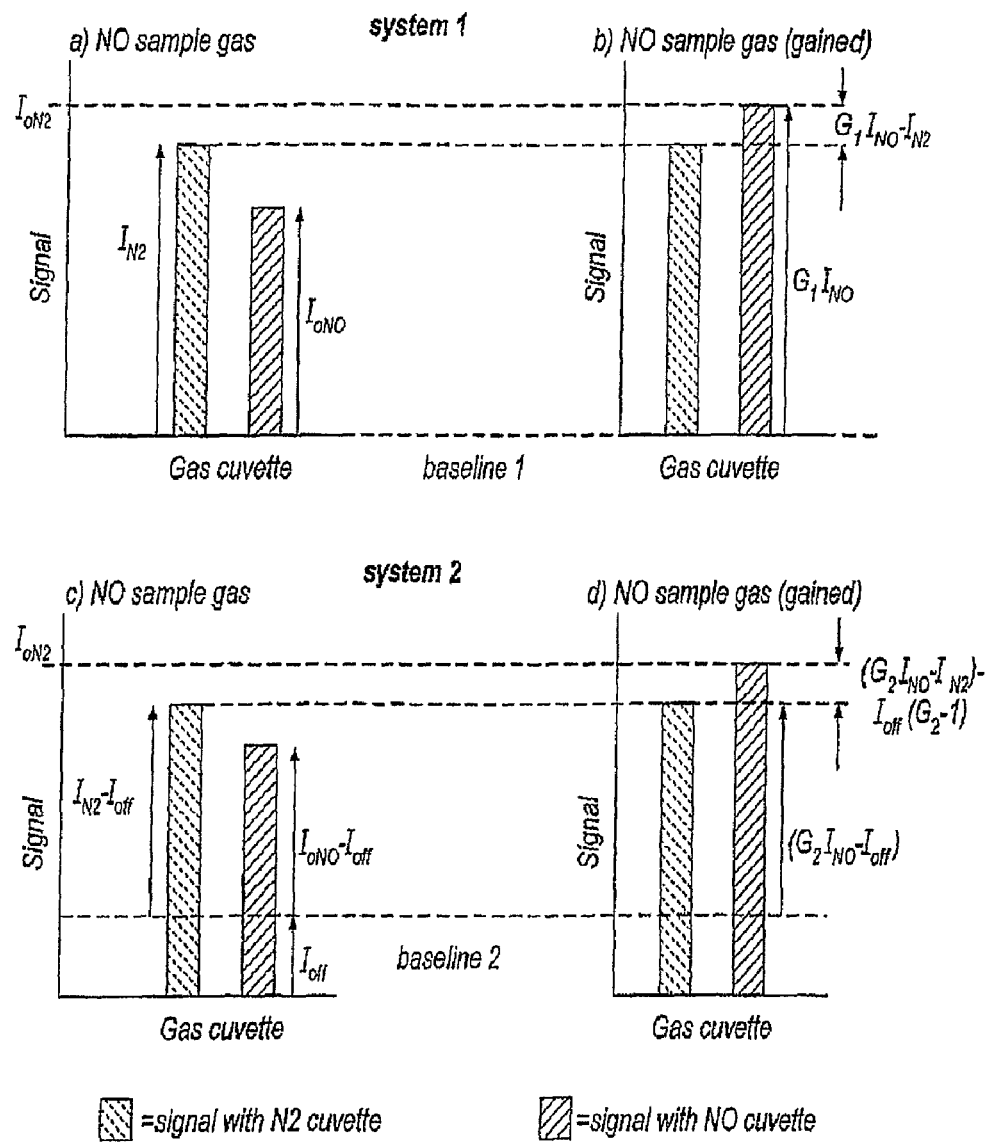
FIGS. 4 and 7 are diagrams aiding the explanation of the preferred method according to the present invention.
Figure 5:
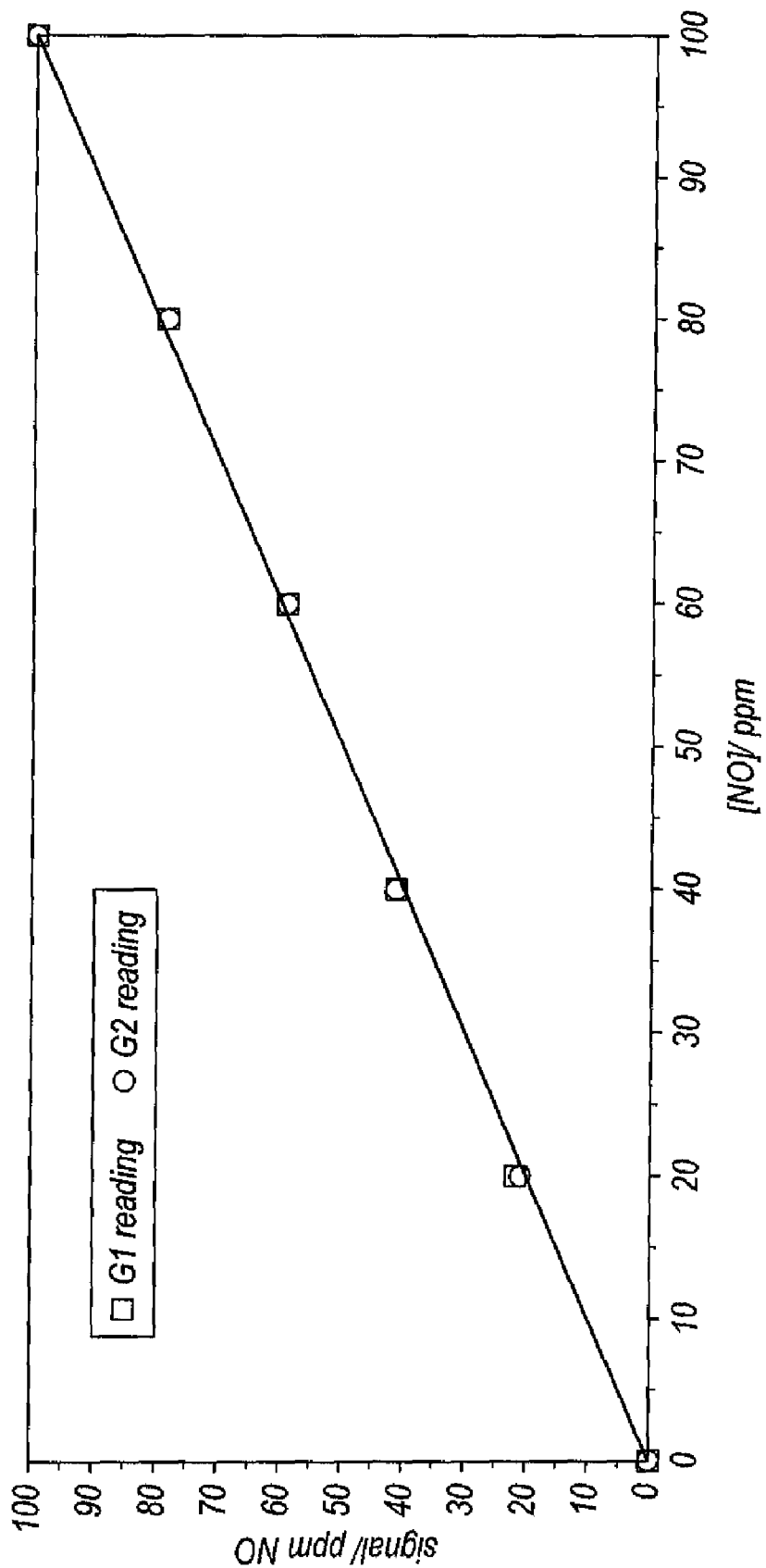

The concept is illustrated in simplified format in FIG. 4. For simplicity, it is assumed that the NO cuvette signal does not change significantly when NO is present in the cell due to pre-adsorption. The two systems 1 and 2 are both equally valid, although they have different gains G1 and G2. Each system can be calibrated independently to give a proportional response to the presence of NO in the sample cell. This is illustrated in FIG. 5.

Figure 6:
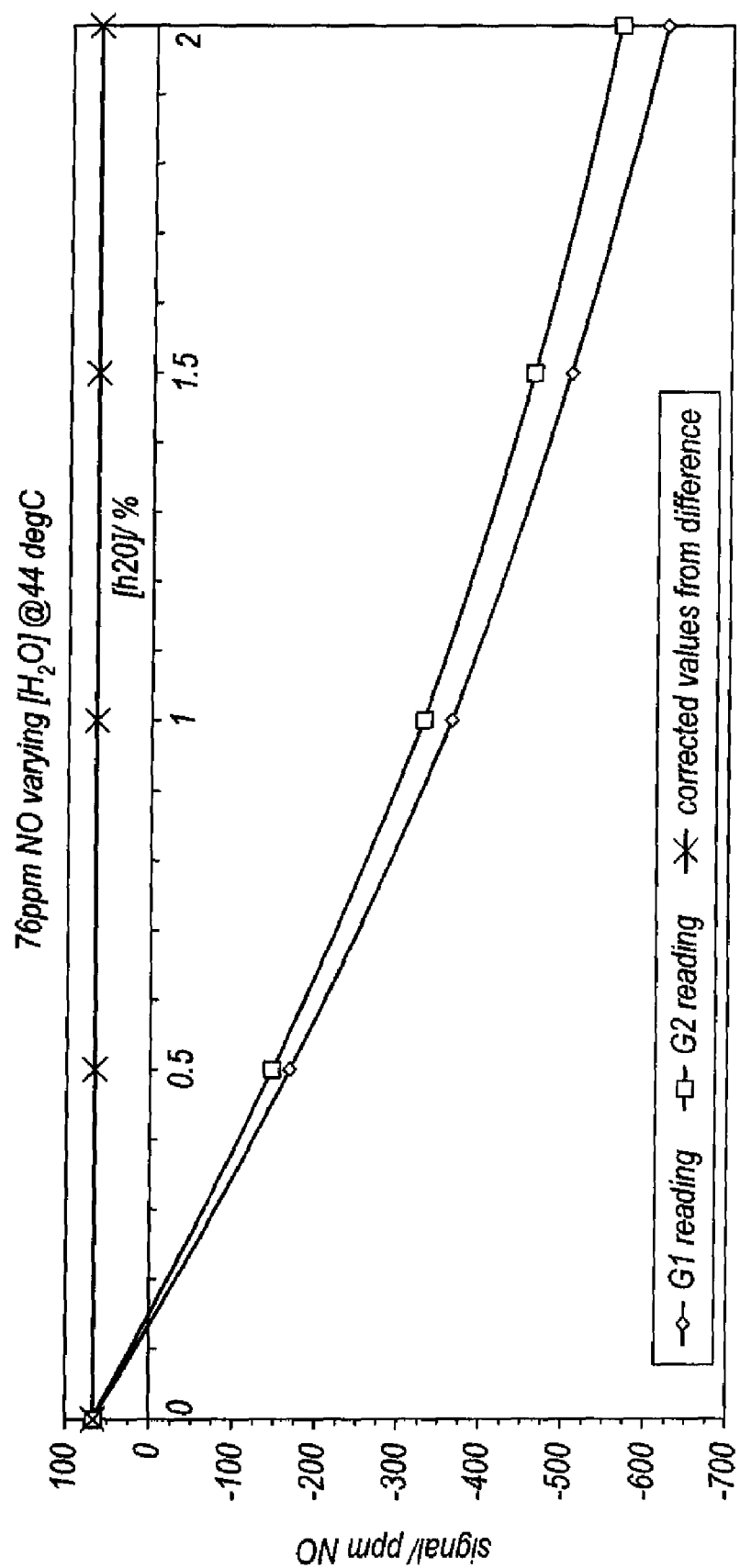
Figure 7:
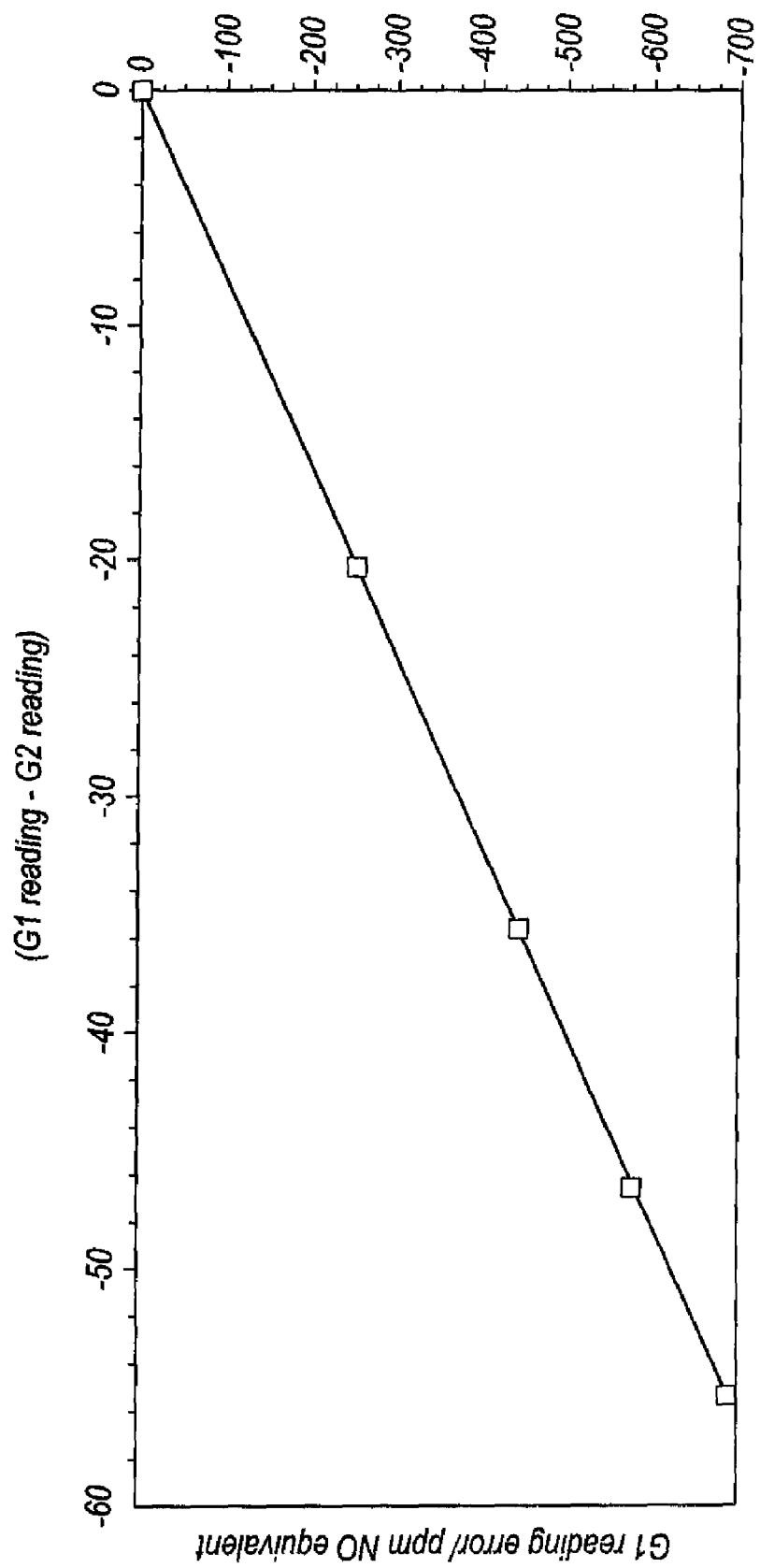

When water is present, an error on the output is seen for both systems with gain G1 and G2. This is shown using experimental results in FIG. 6 for a constant level of 76 ppm NO in nitrogen for increasing levels of water background. Also shown in FIG. 6 is the corrected concentration readings using correction factors from a previous calibration with water (FIG. 7). The concentration of water can also be deduced from the difference in readings and hence a concentration reading could be displayed if required.

This method also applies if a change in the negative cross interference for NO itself in the sample cell occurs with respect to the NO in the sealed cuvette. This might happen, for example, due to line broadening such as that caused by changes in background gas composition and pressure or temperature changes. This would normally result in a measurement error due to a change in the relative NO sensitivity. However, using the method described in this patent, this effect could also be corrected for.

The invention claimed is:

1. A method for automatically compensating for the presence of one or more background interferents in a spectroscopic measurement of a material through analysis of the spectroscopic measurement signal produced by a detector in response to detecting light transmitted through a sample chamber, said method being carried out using optical path gas filter correlation measurements wherein light from a broadband source is modulated using an absorbing gas filter containing a measure gas and a non-absorbing filter containing a reference gas, wherein the light is transmitted to said sample chamber, the method comprising the steps of:
    (a) manipulating artificially induced negative cross interferences in the measurement signal by varying differential gain applied to the signal and taking measurements using two or more baseline references at different non-zero gain levels; and
    (b) determining an auto-correction function from the manipulated measurement signal by determining a degree of mismatch between signals resulting from step (a) during calibration, wherein a change in said mismatch in subsequent measurements is an indication of background interferent concentration.

2. The method according to claim 1, comprising using the determined auto-correction function to generate a corrected measurement signal, thereby to compensate for the effects of the one or more background interferents.

3. The method according to claim 1, comprising monitoring the presence of a first interferent and producing a signal relating to its concentration.

4. The method according to claim 1, comprising monitoring the presence of multiple interferents and producing signals relating to their concentration.

5. The method according to claim 4, wherein a separate absorbing gas filter is used for each of said interferents.

6. The method according to claim 1, using absorption measurements at any wavelength for any medium: solid, liquid, gas or plasma.

7. The method according to claim 1, using reflectance measurements at any wavelength for any medium: solid, liquid, gas or plasma.

8. A method for automatically compensating for the presence of spectral broadening in a spectroscopic measurement of a material through analysis of the spectroscopic measurement signal produced by a detector in response to detecting light transmitted through a sample chamber, said method being carried out using optical path gas filter correlation measurements wherein light from a broadband source is modulated using an absorbing gas filter containing a measure gas and a non-absorbing filter containing a reference gas, wherein the light is transmitted to said sample chamber, the method comprising the steps of:
    (a) manipulating artificially induced negative cross interferences in the measurement signal by varying differential gain applied to the signal, and taking measurements using two or more baseline references at different non-zero gain levels; and
    (b) determining an auto-correction function from the manipulated measurement signal by determining a degree of mismatch between signals resulting from step (a) during calibration, wherein a change in said mismatch in subsequent measurements is an indication of spectral broadening.

9. The method according to claim 8, comprising monitoring the presence of spectral broadening and producing a signal relating to its cause, such as background gas composition, pressure or temperature.

10. The method according to claim 8, using absorption measurements at any wavelength for any medium: solid, liquid, gas or plasma.

11. The method according to claim 8, using reflectance measurements at any wavelength for any medium: solid, liquid, gas or plasma.

* * * * *

UNITED STATES PATENT AND TRADEMARK OFFICE
CERTIFICATE OF CORRECTION

| | | |
|---|---|---|
| PATENT NO. | : 7,751,051 B2 | Page 1 of 1 |
| APPLICATION NO. | : 11/539962 | |
| DATED | : July 6, 2010 | |
| INVENTOR(S) | : James Hobby et al. | |

It is certified that error appears in the above-identified patent and that said Letters Patent is hereby corrected as shown below:

Col. 2, line 46, delete "not possible" and replace with --not be possible--

Col. 3, line 1, delete "FIGS. 4 and 7" and replace with --FIGS. 4 through 7--

Col. 3, line 35, delete "pre-adsorption." and replace with --pre-absorption.--

Signed and Sealed this

Twelfth Day of October, 2010

David J. Kappos
*Director of the United States Patent and Trademark Office*